United States Patent [19]
Robinson et al.

[11] 4,455,388
[45] Jun. 19, 1984

[54] CATALYST AND PROCESS FOR PRODUCING DIOLEFINS

[75] Inventors: Paul R. Robinson, Costa Mesa; Eric L. Moorehead, Diamond Bar, both of Calif.

[73] Assignee: Union Oil Company of California, Los Angeles, Calif.

[21] Appl. No.: 335,531

[22] Filed: Dec. 29, 1981

Related U.S. Application Data

[63] Continuation-in-part of Ser. No. 328,446, Dec. 7, 1981.

[51] Int. Cl.$^3$ ............................................. B01J 27/14
[52] U.S. Cl. .................................... 502/209; 585/623
[58] Field of Search ................................ 252/435, 437

[56] References Cited

U.S. PATENT DOCUMENTS

| | | |
|---|---|---|
| 3,775,508 | 11/1973 | Pitzer . |
| 3,789,078 | 1/1974 | Nolan et al. . |
| 3,856,881 | 12/1974 | Manning . |
| 3,862,146 | 1/1975 | Boghosian . |
| 3,867,411 | 2/1975 | Raffelson et al. . |
| 3,884,835 | 5/1975 | Vaughan ............................ 252/451 |
| 3,888,886 | 6/1975 | Young et al. . |
| 3,914,332 | 10/1975 | Dickason . |
| 3,915,892 | 10/1975 | Harrison . |
| 3,927,138 | 12/1975 | Walker . |
| 3,977,998 | 8/1976 | Freerks et al. . |
| 4,061,724 | 12/1977 | Grose et al. ........................ 423/335 |
| 4,092,269 | 5/1978 | Mount et al. . |
| 4,123,388 | 10/1978 | Kerr et al. . |
| 4,151,116 | 4/1979 | McDermott . |
| 4,153,577 | 5/1979 | Barone . |
| 4,165,299 | 8/1979 | Pedersen . |
| 4,165,300 | 8/1979 | Dolbyj et al. . |
| 4,179,404 | 12/1979 | Barone . |
| 4,206,084 | 6/1980 | Strojny et al. . |
| 4,246,421 | 1/1981 | Bartek et al. ........................ 252/437 |
| 4,270,017 | 5/1981 | Young ................................. 585/437 |
| 4,283,306 | 8/1981 | Herkes ................................ 252/432 |
| 4,309,275 | 1/1982 | Mulaskey ............................ 208/109 |
| 4,309,276 | 1/1982 | Miller .................................. 208/109 |
| 4,314,983 | 2/1982 | Hass et al. ................... 423/573 G X |
| 4,362,653 | 12/1982 | Robinson ........................... 252/455 R |

FOREIGN PATENT DOCUMENTS 35807  9/1981  European Pat. Off. .

OTHER PUBLICATIONS

Silicalite, A New Hydrophobic Crystalline Silica Molecular Sieve, by E. M. Flanigen et al., Nature vol. 271, Feb. 9, 1978.
Reactions on ZSM-5-Type Zeolite Catalysts, by J. R. Anderson et al., Journal of Catalysis 58, 114–130 (1979).
Chemical and Physical Properties of the ZSM-5 Substitutional Series, by D. H. Olson et al., Journal of Catalysis 61, 390–396 (1980).

Primary Examiner—Delbert E. Gantz
Assistant Examiner—William G. Wright
Attorney, Agent, or Firm—Dean Sandford; Gregory F. Wirzbicki; Cleveland R. Williams

[57] ABSTRACT

High surface area oxidative dehydrogenation catalysts which are suitable for converting $C_4$ to $C_8$ monoolefins to diolefins are disclosed, comprising the oxides of an alkali metal, vanadium, phosphorus, potassium and tin in combination with a crystalline silica having a surface area between 30 $M^2/g$ to 450 $M^2/g$ and wherein the vanadium has an average valence in the range of from 3.5 to 4.95.

41 Claims, No Drawings

1

CATALYST AND PROCESS FOR PRODUCING DIOLEFINS

RELATED APPLICATIONS

This application is a continuation-in-part application of application, Ser. No. 328,446, filed Dec. 7, 1981.

BACKGROUND OF THE INVENTION

1. Field of the Invention

The present invention relates to oxidative dehydrogenation catalysts, and more particularly to crystalline silica oxidative dehydrogenation catalysts which are useful for producing diolefins from $C_4$ to $C_8$ mono-olefins.

2. The Prior Art

The use of dehydrogenation catalysts to oxidize hydrocarbons to diolefins is known and appreciated by the prior art. For example, U.S. Pat. No. 3,927,138 relates to a process for producing diolefins from paraffins, especially the dehydrogenation of butane to butenes and butadiene, using an oxidation catalyst consisting of a ferrous metal, tin, phosphorus and an alkali metal. The catalysts may be supported on or diluted with materials such as silica, alumina, boria, etc.

U.S. Pat. No. 3,914,332 discloses a process for the oxidative dehydrogenation of butane to a mixture of butenes and butadiene using a vanadium-potassium-sulfur catalyst supported on silica, which permits the use of high space velocities.

U.S. Pat. No. 3,856,881 relates to a process for the dehydrogenation of $C_4$ to $C_5$ hydrocarbons to produce the corresponding dehydrogenated compounds. The dehydrogenation catalyst used consists of a crystalline spinel of a phosphorus and divalent-metallic vanadium compound. Catalyst carriers such as alumina, pumice, silicon, etc. are additionally described as suitable for use in the dehydrogenation catalyst.

U.S. Pat. No. 3,789,078 discloses a dehydrogenation process and dehydrogenation catalysts which are useful for oxidatively dehydrogenating organic compounds such as alkenes, alkadienes, cycloalkenes, alkylpyidines and alkyl aromatics. The catalyst consists of a combination of phosphorus, tin and a Group IA or IIA metal of the Periodic Table. Substantially any phosphorus, tin and Group IA or IIA containing materials may be employed in the catalyst so long as at least one of the materials used contains oxygen.

U.S. Pat. No. 3,775,507 relates to an oxidative dehydrogenation process for dehydrogenating $C_2$ to $C_{10}$ alkenes, alkadienes, etc. using an oxidation catalyst consisting of phosphorus, tin and a Group IA or IIA metal of the Periodic Table. The catalyst is improved by including a heat-volatile activity-stimulating ammonium salt in the catalyst composition prior to the catalyst particle-forming stage.

As can readily be determined from the above, there is an ongoing effort to develop oxidative dehydrogenation catalysts for producing diolefins from alkanes and mono-olefins.

Accordingly, it is an object of the present invention to provide an oxidative dehydrogenation catalyst for producing diolefins from mono-olefins.

Another object of the present invention is to provide an oxidative dehydrogenation catalyst having a large surface area which is useful for producing butadiene and to provide a method of preparing the same.

A further object of the present invention is to provide a method for obtaining improved yields and selectivity of diolefins, for example, butadiene.

These and other objects are accomplished according to the present invention by oxidizing a $C_4$ to $C_8$ mono-olefin to the corresponding diolefin in the presence of an alkali metal promoted oxidative dehydrogenation catalyst comprising the oxides of an alkali metal, vanadium, phosphorus and tin on a crystalline silica support.

SUMMARY OF THE INVENTION

The present invention resides in an oxidative dehydrogenation catalyst described by the formula:

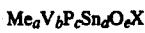

$$Me_aV_bP_cSn_dO_eX$$

wherein X is a crystalline silica, Me is an alkali metal, a is 0.10 to 2, b is 0.10 to 1, c is 1, d is 0.001 to 0.30 and e is a number which satisfies the valence requirements of the other elements present.

The invention additionally resides in a method of preparing an alkali metal promoted, vanadium, phosphorus, tin, mixed-oxide, crystalline silica, oxidative dehydrogenation catalyst which comprises:

(A) reacting an alkali metal containing compound, a vanadium compound and a phosphorus compound in an acidic aqueous solution with a tin compound under reaction conditions which will provide vanadium having an average oxidation state of 3.50 to 4.95 to form a catalyst precursor, (B) admixing the catalyst precursor with a binder, solvent and crystalline silica to form an impregnated crystalline silica, and (C) Calcining the oxidation catalyst at temperatures in the range of from 400° F. to 1,200° F., for ¼ hour to 6 hours.

A method for producing diolefins or conjugated dienes is disclosed which comprises reacting a $C_4$ to $C_8$ mono-olefin with a gas containing helium and molecular oxygen in the vapor phase, under reaction conditions and in the presence of an oxidative dehydrogenation catalyst described by the formula:

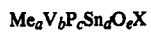

$$Me_aV_bP_cSn_dO_eX$$

wherein X is a crystalline silica, Me is an alkali metal, a is 0.10 to 2, b is 0.10 to 1, c is 1, d is 0.001 to 0.30, and e is a number which satisfies the valence requirements of the other elements present.

DETAILED DESCRIPTION OF THE INVENTION

Broadly described, the catalysts of this invention have the general formula:

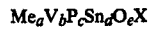

$$Me_aV_bP_cSn_dO_eX$$

wherein X is a crystalline silica, Me is an alkali metal, a is 0.10 to 2, b is from 0.10 to 1, c is 1, and d is from 0.001 to 0.30. The above formula is not an empirical formula, however, the numbers assigned to the subscript letters, i.e., a,b,c and d represent the atomic ratio of the respective Me, V, P and Sn active components of the catalyst. The e in the above formula may vary widely depending on the mixed oxide combination within the catalyst complex. The only restriction of the e value is that the number assigned to e must satisfy the valency requirements of the other elements in the catalyst complex.

Generally, oxygen combines with the alkali metal, vanadium, phosphorus and tin to form a catalyst precursor which is an oxygen complex or the oxides of these compounds. The oxygen content of the catalyst precursor will vary depending upon the relative stoichiometry of the potassium, vanadium, phosphorus and tin present. However, e will normally have a value of from 2 to 12, preferably from 2.5 to 8.

One disadvantage of using acidic catalysts to produce diolefins from mono-olefins is that basic products have a tendency to remain on the catalyst surface and react further. Thus, a reaction to produce diolefins from mono-olefins and alkanes would, under these circumstances, proceed to a more acid product, for example, maleic anhydride from butene or butane. This problem is solved by the addition of an alkali metal promoter to the acidic dehydrogenation catalyst to render said catalyst less acidic. Although the invention is not limited to any theory, it is believed that a basic product or molecule, for example, 1,3 butadiene when butene is the feed source, will desorb from said catalyst rather than remain on the catalyst surface to react further and produce an acidic product or compound. This concept may be further described by the fact that the energy required to remove an electron (the ionization potential) from a basic molecule is smaller than the energy similarly required from an acid molecule. Selective oxidation reactions can therefore be classified into various types, depending on the ionization potential of the hydrocarbon reaction and of the hydrocarbon product. For example, the reaction of butene to butadiene may be classified as a basic to basic type reaction, while the reaction of butadiene to maleic anhydride may be classified as a basic to acidic type reaction. For the basic to basic or mono-olefin to diolefin reaction to proceed, there must be cooperative action between both acidic and basic sites on the catalyst. For example, basic reactant molecules are dissociatively absorbed on acidic sites which extract a hydrogen atom as $H^-$ and thus generate an allyl radical. The radical moves to a neighboring basic site where it loses a second hydrogen and is partially oxidized to the resulting basic product. The product, being basic, easily desorbs from the basic site. Oxygen near the basic site is replaced by an oxygen atom of the catalyst lattice which is near an acidic site, and the oxygen of the gaseous phase replenishes the latter. Thus, good selectivities for reactions of the basic to basic type need both acidic and basic sites on the catalyst surface.

Alkali metals which are suitable as promoters herein include lithium, sodium, potassium, rubidium and cesium. The preferred alkali metal is potassium. Suitable alkali metal compounds useful as a source of alkali metals are selected from alkali metal salts such as the phosphates, i.e., meta, ortho, pyro, tri etc., the carbonates, chlorides, oxalates and acetates. An especially desirable alkali metal compound is potassium meta phosphate.

Vanadium compounds useful as a source of vanadium in the catalyst precursor are those vanadium compounds known to the art. Suitable vanadium compounds include vanadium salts, such as ammonium metavanadate and vanadyl sulfate; vanadium oxides, such as vanadium pentoxide; and vanadium oxyhalides, such as vanadium oxytrichloride. However, pentavalent vanadium compounds such as ammonium metavanadate and vanadium pentoxide are preferred.

Phosphorus compounds useful as a source of phosphorus in the catalyst precursor are also those known to the art. Suitable phosphorus compounds are selected from phosphoric acid, phosphorus pentoxide, ammonium phosphate and diammonium phosphate. The preferred phosphorus compounds are pentavalent phosphorus compounds such as phosphoric acid and phosphorus pentoxide.

Suitable tin compounds are those tin compounds which have a valence of $+2$, since the tin compound acts as a reducing agent for the vanadium compound in the catalyst. Tin compounds useful herein preferably are selected from stannous chloride, stannous fluoride, stannous bromide, stannous oxide, stannous sulfate, stannous acetate, stannous pyrophosphate, and stannous oxalate. Upon reaction of the tin compound with the vanadium compound, tin $+2$ (stannous) will be oxidized up to the tin $+4$ (stannic) oxidation state and vanadium in the $+5$ oxidation state will be reduced to an average oxidation state of less than $+5$.

The catalyst precursor is preferably produced by dissolving and mixing compounds containing an alkali metal, vanadium, phosphorus and tin in an acidic-aqueous medium such as water and hydrochloric acid, hydoiodic acid, hydroformic acid, acetic acid, oxalic acid, maleic acid, citric acid or formic acid. The alkali metal-vanadium-phosphorus-tin compounds are contacted at an atomic ratio of alkali metal-vanadium-phosphorus-tin of from 0.10:0.10:1:0.001 to 2:1:1:0.30, preferably from 0.4:0.20:1:0.002 to 1:1:1:0.20. The atom ratio of vanadium to phosphorus in the starting material is important since it controls the vanadium to phosphorus atom ratio in the final catalyst. When the oxidation catalysts herein contain a vanadium-phosphorus atom ratio below 0.10:1 or above 1.00, the yield of diolefin using these catalysts is so low as to render the reaction commercially unattractive. It should be noted that phosphorus aids in stabilizing vanadium in the final catalyst composition, the alkali metal compoun renders the catalyst surface basic which favors production of diolefins from mono-olefins, while tin $+2$ acts as a reducing agent which aids in the reduction of vanadium to a valence state of less than $+5$. It should additionally be noted that the above-described acids which dissolve the alkali metal, vanadium, phosphorus and tin compounds act as reducing agents for the vanadium compounds. However, the reduction process takes from one-half hour to about one hour when tin is not present in the reaction medium. Upon the addition of tin to the reaction medium, the reduction of vanadium to a valence of less than $+5$ takes place almost instantly, i.e., less than one minute. Generally, the vanadium is reduced to an average valance within the range of from $+3.50$ to $+4.95$, preferably from $+4.10$ to $+4.70$.

Conventional apparatus and techniques known to the art may be used to dissolve and react the components which make up the catalyst precursor. For example, temperatures of from 100° F. to 220° F., preferably from 180° F. to 220° F. and a reaction time of from ¼ hour to 6 hours under atmospheric pressure normally are sufficient to dissolve and react the alkali metal, vanadium, phosphorus and tin compounds. However, pressures from atmospheric pressure to 50 p.s.i.g. may be used to shorten the dissolution and reaction times. Generally, agitation is supplied during the reaction period to ensure complete contact of the reactants.

After the reaction proceeds to completion the catalyst precursor is concentrated and collected using conventional methods and techniques and admixed with a crystalline silica to form an impregnated crystalline silica.

The crystalline silica in this invention is analogous to highly siliceous alkali silicas which form as insoluble compounds during extended hydrothermal digestion. The organic agent in the form of a nitrogen compound incorporated as a cation during crystallization of the crystalline silica herein becomes a source of micropores when eliminated by combustion or extraction. The surface of these micropores are relatively free of hydroxyl groups. The isolated hydroxyl groups which are present provide a moderate acidic strength when the crystalline silica is thermally activated. The crystalline silica is a unique, active solid which is suitable for use as a catalyst component or in catalysts used in hydrocarbon reactions.

The crystalline silica provides not only the required surface for the catalyst precursor, but gives physical strength and stability to the catalyst material. In addition, the crystalline silica has a large surface area upon which the catalyst precursor is deposited.

The crystalline silica composition (i.e. silicalite) herein is characterized by uniform pore dimensions of approximately 6 Å and is prepared by calcining a crystalline hydrated alkylonium silica prepared by hydrothermal crystallization from a reaction mixture containing as essential reagents, water, amorphous silica and a quaternary ammonium compound, for example, tetraethyl ammonium hydroxide, at a pH of at least 10. The compound thus formed is calcined to decompose the alkylonium moieties present. The crystalline silica exhibits no ion exchange properties; however, because of its uniform pore structure it is capable of making size-selective separations of molecular species. A more detailed description of how to prepare the crystalline silica herein is disclosed in U.S. Pat. No. 4,061,724, which is incorporated herein by reference in its entirety.

The crystalline silica, produced from the above-described mixture, has a topological type of tetrahedral framework, which contains a large fraction of five-membered rings of silica-oxygen tetrahedra. The framework comprises a three-dimensional system of intersecting channels which are defined as ten rings of oxygen atoms extending in three directions. Precursor-organic nitrogen ions which occupy the intersecting channels, are removed by heating or in the alternative, by extracting with an acid to yield the desired crystalline silica. The resulting void volume occupies approximately 33 percent of the crystal structure, and the three-dimensional channel is wide enough to absorb organic molecules having up to about 6 Å in diameter. The crystalline silica, herein, degrades to glass products and dense crystalline silica above about 2,732° F.

Generally, from 15 to 50 weight percent of the catalyst precursor comprising the oxides of an alkali metal vanadium, phosphorus and tin is mixed with from 50 to 85 weight percent of the crystalline silica. Binding agents and additives may optionally be added to the catalyst to provide the proper consistency of the catalyst prior to mixing and forming said catalyst. The binding agents and additives, when used, preferably comprise from 0.1 to 10, especially from 3 to 10 weight percent of the finished catalyst. Suitable agents include methyl cellulose, silica, and alumina. Additives suitable for use herein include organic polar solvents such as ethanol, propanol, isopropanol, butanol, etc. The binding agents and additives are normally mixed in a weight ratio of from 1:20 to 20:1. The preferred method of mixing the catalyst precursor and crystalline silica is by comulling. However, other conventional mixing techniques may be used.

The physical form of the catalysts of this invention depends to a large extent upon the technique of drying and/or the desired shape. The catalysts may be produced as spheres, pellets, beads, elongated cylinders, and three-lobe or cloverleaf configurations. For example, the composites may be filtered and oven dried, and course granules may be obtained by breaking up and sieving the oven-dried cake up to any desired size. Spray drying the catalyst, so that the dried catalyst will pass through 4 to 200 mesh sieve (U.S.) is another method of producing the desired catalyst. Another method involves shapeboring the catalyst into a desired configuration using a restraint to maintain the desirable shape in a cylindrical configuration having a diameter of from 1/16 to ⅛ inch and a length of from ¼ inch to 178 inch.

The final catalyst is activated by calcination which preferably is performed in an air or oxygen atmosphere at a temperature of from about 400° F. to about 1,200° F., for about ¼ hour to about 6 hours, preferably from about ½ hour to about 4 hours.

The catalyst thus produced is especially suited for oxidizing $C_4$ to $C_8$ mono-olefins to the corresponding diolefins and has a surface area of from 30 $M^2/g$ to 450 $M^2/g$, a pore volume of from 0.1 cc/g to 0.8 cc/g and a compacted bulk density of from 0.35 to 1.50 g/cc.

A variety of reactors may be used in the oxidation process herein. For example, conventional fluidized bed reactors and fixed-bed or tube, heat exchanger type reactors are satisfactory; the details of the operation of such reactors are well known to those skilled in the art. The oxidation reaction is an exothermic reaction, necessitating relatively close control of the reaction temperature. It is desirable to have the surface of the reactor at a constant temperature and some medium may be necessary to conduct heat away from the reactor to aid temperature control. Examples of desirable media include molten sulfur, mercury, molten lead, or eutectic salt baths, for example a sodium nitrate-nitrate eutectic constant temperature mixture. An additional method of temperature control is the use of a metal block reactor whereby the metal surrounding the reactor chamber acts as a temperature regulating body. Conventional heat exchangers may also be used.

Normally a reaction mixture of a gaseous feed stream comprising a $C_4$ to $C_8$ mono-olefin and a molecular oxygen containing gas, for example, air, a mixture of air and oxygen, mixtures of carbon dioxide and oxygen or mixtures of nitrogen or steam with air or oxygen is charged to a reaction zone, for example, a conventional pressure reactor. The gaseous feed stream generally will contain a molecular oxygen containing gas and from about 0.1 to about 5 mole percent, especially from about 0.1 to about 3 mole percent, preferably from about 0.1 to about 2.5 mole percent of a $C_4$ to $C_8$ mono-olefin for optimum yield of the corresponding diolefin. Although higher concentrations of mono-olefin may be employed, they are not recommended because explosive hazards may be encountered. It should additionally be noted that an inert gas, for example helium, nitrogen, argon, etc., may be employed as a carrier in the process herein without deleterious effect upon the oxidative dehydrogenation reaction. Normally, the inert gas, molecular oxygen and $C_4$ to $C_8$ mono-olefin are introduced into a reactor at a molar ratio range of from 4:1:0.001 to 4:1:0.10, preferably from 4:1:0.01 to 4:1:0.08.

Olefins which may be used to produce diolefins are selected from mono-olefins containing 4 to 8 carbon atoms, for example, desirable olefins include butene, pentene, cyclopentene, hexene, cyclohexene, heptene, cycloheptene, octene, or a mixture thereof.

Preferably the gaseous feed stream comprising molecular oxygen and a $C_4$ to $C_8$ mono-olefin is reacted in the presence of an oxidation catalyst described by the formula:

$$Me_aV_bP_cSn_dO_eX$$

wherein X is crystalline silica, Me is an alkali metal, a is 0.1 to 2, b is 0.1 to 1, c is 1, d is 0.001 to 0.30 and e is a number which satisfies the valence requirements of the other elements present. The flow rate of the gaseous feed stream through the pressure reactor may be varied within rather wide limits but a preferred flow rate consists of a gas hourly space velocity (GHSV) of from 2,400 to 6,000 reciprocal hours.

The temperature of reaction may be varied herein, but normally the reaction should be conducted at temperatures within a rather critical range. The overall temperature range for the conversion of $C_4$ to $C_8$ mono-olefins to the corresponding diolefins preferably is from 500° F. to 760° F., especially from 600° F. to 700° F.

Typically, the reaction pressure is from atmospheric pressure to 200 p.s.i.g., preferably from atmospheric pressure to 50 p.s.i.g., and as previously stated, the reaction may be carried out in any reactor suitable for effecting vapor phase oxidation reactions, but preferably a fixed catalyst bed reactor is employed.

The invention is further illustrated by the following examples which are illustrative of various aspects of the invention and are not intended as limiting the scope of the invention as defined by the appended claims.

EXAMPLE I

An oxidative dehydrogenation catalyst having an average oxidation state of 4.46 for vanadium is prepared by charging 14.0 grams (0.12 moles) of ammonium metavanadate, 1.8 grams (0.008 moles) of stannous chloride, 50 ml of distilled water, 10 ml of ethanol and 11 ml of concentrated hydrochloric acid to an 800 ml round bottom flask equipped with a water cooled condensor, heating mantle and magnetic stirrer. The above-described mixture turns green. Next, 33.04 grams (0.280 moles) of potassium metaphosphate, 15 ml of distilled water and 2.79 grams (0.028 moles) of 85 percent phosphoric acid are introduced into the flask. This mixture is heated to a temperature of 122° F. and agitated with a magnetic stirrer for 18 hours.

The non-homogeneous mixture is mixed with 8.0 grams of silica, 100 grams of crystalline silica (silicalite), air-dried at 230° F. for 12 hours, and then calcined in air at 932° F. for 3 hours. The resulting catalyst is screened to give an 80–200 mesh (U.S.) catalyst particle size. The catalyst has a surface area of 203 $M^2/g$ and a potassium-vanadium-phosphorus-tin atomic ratio of 0.91:0.39:1.0:0.026.

EXAMPLE II

An oxidative dehydrogenation catalyst having an average oxidation state of 4.36 for vanadium and a surface area of 247 $M^2/gram$ is prepared by charging 14.0 grams (0.120 mole) of ammonium metavanadate, 1.8 grams (0.008 mole) of stannous chloride, 50 ml of distilled water, 10 ml of ethanol and 11 ml of concentrated hydrochloric acid to an 800 ml round bottom flask equipped with a water cooled condensor, heating mantle and magnetic stirrer. Then, 18 grams (0.153 mole) of potassium metaphosphate, 15 ml of distilled water and 16.5 grams (0.168 moles) of 85 percent phosphoric acid are introduced into the flask. The mixture is heated to a temperature of 122° F. and agitated with a magnetic stirrer for 12 hours.

The dark green slurry produced above is co-mulled with 8.0 grams of silica and 120 grams of crystalline silica (silicalite) using a model no. 472 Lancaster Mixer, manufactured by Posey Iron Works, Inc. of Lancaster, Pa. The mixer is operated at 36 RPM. The resulting slurry is calcined in air at 932° F. for 3 hours. The catalyst thus formed has a potassium-vanadium-phosphorus-tin atomic ratio of 0.48:0.37:1.0:0.025.

EXAMPLE III

An oxidative dehydrogenation catalyst having an average oxidation state of 4.65 for vanadium and a surface area of 276 $M^2/g$ is prepared in accordance with the procedure used in Example II with the following exceptions:

3.30 grams (0.028 mole) of potassium metaphosphate and 27.4 grams (0.280 mole) of phosphoric acid are utilized. The resulting catalyst has a potassium-vanadium-phosphorus-tin atomic ratio of 0.091:0.39:1.0:0.26.

EXAMPLE IV TO VI 1, 3 butadiene is produced from butene by charging 1 cc (0.53 grams) of the catalyst of Example I to a continuous flow catalytic reaction system equipped with programmable gas chromatograph and marketed commercially under the trade name Flow Diagram S Chematic-CDS 800 CF-HP/GC Catalytic Reaction System, by the Chemical Data Systems, Inc., Oxford, Pa. The reactor is a downflow tubular reactor having a length of 9 inches, an outside diameter of ⅜ inch, an inside diameter of ¼ inch. In addition, the reactor is equipped with a 1/16 inch outside diameter, central-longitudinal thermowell. A feed stream comprising 74.5 volume percent helium, 24.5 volume percent oxygen and 0.53 volume percent 1-butene is charged to the reactor at a rate of 0.16 standard cubic feet (SCF) hour. The Gas Hourly Space Velocity (GHSV) is 4,500 reciprocal hours at atmospheric pressure and the catalyst bed temperature is as indicated in Table 1 below. In addition, the selectivity and yield in Table 1 are reported as mole percent.

TABLE I

| Example | Temperature (°F.) | Butene Conversion (%) | Butadiene Selectivity (%) | Yield (%) |
| --- | --- | --- | --- | --- |
| IV | 660 | 70 | 75 | 52.50 |
| V | 665 | 60 | 75 | 45.00 |
| VI | 670 | 65 | 81 | 52.65 |

The above data indicate that the oxidative dehydrogenation catalysts herein is highly selective in producing diolefins from mono-olefins.

EXAMPLE VII

Butene is selectively oxidized to 1, 3 butadiene by charging 1 cc (0.53 gram) of the catalyst of Example II to a continuous flow catalytic reaction system equipped with programmable gas chromatograph and marketed commercially under the trade name Flow Diagram S Chematic-CDS 800 CF-HP/GC Catalytic Reaction System, by the Chemical Data Systems, Inc., Oxford, Pa. The reactor is a downflow tubular reactor having a length of 9 inches, an outside diameter of ⅜ inch, an inside diameter of ¼ inch. In addition, the reactor is equipped with a 1/16 inch outside diameter, central-longitudinal thermowell. A feed stream comprising 74.5 volume percent helium, 24.5 volume percent oxygen and 0.53 volume percent of butene-1 is charged to the reactor at a rate of 0.16 standard cubic feet (SCF) 1 hour. The Gas Hourly Space Velocity (GHSV) is 4,500 reciprocal hours at atmospheric pressure and the temperature is 670° F. Analysis indicates that 75.70 percent of the butene is converted to 1,3 butadiene, with a selectivity of 70 mole percent and a yield of 52.50 mole percent.

As can readily be determined from the above Examples, the dehydrogenation catalysts herein effectively convert mono-olefins, for example, 1-butene to diolefins such as, 1,3-butadiene under the described reaction conditions. Obviously, many modifications and variations of the invention, as hereinbefore set forth, may be made without departing from the spirit and scope thereof, and therefore only such limitations should be imposed as are indicated in the appended claims.

We claim:

1. An oxidative dehydrogenation catalyst defined by the formula:

$$Me_a V_b P_c Sn_d O_e X$$

wherein X is crystalline silica, Me is an alkali metal, a is 0.10 to 2, b is 0.10 to 1, c is 1, d is 0.001 to 0.30 and e is a number which satisfies the valence requirements of the other elements present.

2. The oxidative dehydrogenation catalyst defined in claim 1 wherein the vanadium has an average oxidation state between +3.5 and +4.95.

3. The oxidative dehydrogenation catalyst defined in claim 1 wherein Me is a member selected from the roup consisting of lithium, sodium, potassium, rubidium, or cesium or a mixture thereof.

4. The oxidative dehydrogenation catalyst defined in claim 1 wherein from 15 to 50 weight percent of Me, V, P, Sn, and O as the metal oxides are combined with from 50 to 85 weight percent of X.

5. The oxidative dehydrogenation catalyst defined in claim 1 including from 0.1 to 10 weight percent of a binder selected from the group consisting of silica, methyl cellulose and alumina, and mixtures thereof.

6. The oxidative dehydrogenation catalyst defined in claim 1 having a surface area of from 30 $M^2/g$ to 450 $M^2/g$, a pore volume of from 0.1 cc/g to 0.8 cc/g, and a compacted bulk density of from 0.35 g/cc to 1.50 g/cc.

7. The oxidative dehydrogenation catalyst defined in claim 1 wherein the crystalline silica is silicalite.

8. An oxidative dehydrogenation catalyst defined by the formula:

$$K_a V_b P_c Sn_d O_e X$$

wherein X is silicalite, a is 0.10 to 2, b is 0.10 to 1, c is 1, d is 0.001 to 0.30, and e is a number which satisfies the valence requirements of the other elements present, vanadium has an average oxidation state between 3.50 and 4.95, wherein said dehydrogenation catalyst contains from 15 to 50 weight percent of K, V, P, Sn and O as the metal oxides, from 50 to 85 weight percent of X and from 0.1 to 10 weight percent of a binder selected from the group consisting of silica, methyl cellulose and alumina and mixtures thereof, said oxidative dehydrogenation catalyst having a surface area of from 30 $M^2/g$ to 450 $M^2/g$, a pore volume of from 0.1 cc/g to 0.8 cc/g, and a compacted bulk density of from 0.35 g/cc to 1.50 g/cc.

9. An oxidative dehydrogenation catalyst comprising promoters of one or more alkali metals, vanadium, phosphorus and tin in combination with crystalline silica, said promoters being present in an alkali metal, vanadium, phosphorus and tin ratio between about 0.10:0.10:1:0.001 and 2:1:1:0.30.

10. The oxidative dehydrogenation catalyst defined in claim 9 wherein the alkali metal is lithium, sodium, potassium, rubidium or cesium or a mixture thereof.

11. The oxidative dehydrogenation catalyst defined in claim 9 wherein the crystalline silica is silicalite.

12. The oxidative dehydrogenation catalyst defined in claim 10 wherein the crystalline silica is silicalite.

13. A method of preparing an alkali metal, vanadium, phosphorus, tin, oxygen and crystalline silica, oxidative dehydrogenation catalyst which comprises:
   (A) contacting an alkali metal, a vanadium compound, and a phosphorus compound with an acidic-aqueous medium and a divalent tin compound under reaction conditions which will provide vanadium having an average oxidation state of from +3.50 to +4.95 to form a catalyst precursor;
   (B) admixing the catalyst precursor with crystalline silica, to form an impregnated crystalline silica; and
   (C) calcining the oxidative dehydrogenation catalyst at temperatures in the range of from 400° F. to 1,200° F. for from ¼ hour to 6 hours.

14. The method defined in claim 13 wherein the oxidation catalyst contains an alkali metal, vanadium, phosphorus and tin in an atomic ratio of from 0.10:0.10:1:0.001 to 2:1:1:0.30.

15. The method defined in claim 13 wherein from 15 to 50 weight percent of the catalyst precursor is mixed with from 50 to 85 weight percent of crystalline silica.

16. The method defined in claim 13 wherein the alkali metal is lithium, sodium, potassium, rubidium or cesium or a mixture thereof.

17. The method defined in claim 13 wherein the vanadium compound is a member selected from the group consisting of ammonium vanadate, vanadyl sulfate, vanadium pentoxide and vanadium oxytrichloride, and mixtures thereof.

18. The method defined in claim 13 wherein the phosphorus compound is a member selected from the group consisting of phosphoric acid, phosphorus pentoxide, ammonium phosphate and diammonium phosphate, and mixtures thereof.

19. The method defined in claim 13 wherein the tin compound is stannous chloride, stannous fluoride, stannous bromide, stannous oxide, stannous sulfate, stannous acetate, stannous pyrophosphate, or stannous oxalate, or a mixture thereof.

20. The method defined in claim 13 wherein the acidic-aqueous medium comprises water and an acid selected from the group consisting of hydrochloric acid, hydroiodic acid, hydroformic acid, acetic acid, oxalic acid, maleic acid, citric acid or formic acid, or a mixture thereof.

21. The method defined in claim 13 including mixing from 3 to 10 weight percent of a binding agent and solvent in a weight ratio of from 1:20 to 20:1, with the catalyst precursor and crystalline silica in step (B).

22. The method defined in claim 21 wherein the binding agent is a member selected from the group consisting of silica, methyl cellulose and alumina, and mixtures thereof.

23. The method defined in claim 21 wherein the solvent is a member selected from the group consisting of ethanol, propanol, isopropanol, and butanol, and mixtures thereof.

24. The method defined in claim 13 wherein the reaction conditions comprise temperatures from 100° F. to 220° F. and pressures from atmospheric pressure to 50 p.s.i.g.

25. The method defined in claim 13 wherein the oxidative dehydrogenation catalyst has a surface area of from 30 $M^2/g$ to 450 $M^2/g$, a pore volume of from 0.1 cc/g to 0.8 cc/g, and a compacted bulk density of from 0.35 g/cc to 1.50 g/cc.

26. The method described in claim 13 wherein the crystalline silica is silicalite.

27. The method described in claim 15 wherein the crystalline silica is silicalite.

28. The method described in claim 21 wherein the crystalline silica is silicalite.

29. A method of preparing an alkali metal, vanadium, phosphorus, tin, oxygen and crystalline silica dehydrogenation catalyst which comprises:
 (A) contacting an alkali metal, a pentavalent vanadium compound, a pentavalent phosphorus compound and a divalent tin compound, at an atomic ratio of from 0.10:0.10:1:0.001 to 2:1:1:0.30 with an acidic-aqueous medium at a temperature of from 100° F. to 220° F., and a pressure of from atmospheric pressure to 50 p.s.i.g., to form a catalyst precursor and produce vanadium having an average oxidation state of from +3.50 to +4.95.
 (B) mixing from 15 percent to 50 weight percent of said catalyst precursor with from 50 weight percent to 85 weight percent of crystalline silica to form an impregnated crystalline silica; and
 (C) calcining the dehydrogenation catalyst at temperatures in the range of from 400° F. to 1,200° F., for ¼ hour to 6 hours.

30. The method defined in claim 29 wherein the alkali metal is a member selected from the group consisting of lithium, sodium, potassium, rubidium, and cesium and mixtures thereof.

31. The method defined in claim 29 wherein the vanadium compound is a member selected from the group consisting of ammonium vanadate, vanadyl sulfate, vanadium pentoxide, and vanadium oxytrichloride, and mixtures thereof.

32. The method defined in claim 29 wherein the phosphorus compound is a member selected from the group consisting of phosphoric acid, phosphorus pentoxide, ammounium phosphate, and diammonium pnosphate, and mixtures thereof.

33. The method defined in claim 29 wherein the tin compound is stannous chloride, stannous fluoride, stannous bromide, stannous oxide, stannous sulfate, stannous acetate, stannous pyrophosphate, or stannous oxalate, or a mixture thereof.

34. The method defined in claim 29 wherein the acidic-aqueous medium consists of water and an acid selected from the group consisting of hydrochloric acid, hydroiodic acid, hydroformic acid, acetic acid, oxalic acid, maleic acid, citric acid or formic acid, or a mixture thereof.

35. The method defined in claim 29 including admixing from 0.1 to 10 weight percent of a binding agent and solvent in a weight ratio of from 1:20 to 20:1 with the catalyst precursor and crystalline silica in step (B).

36. The method defined in claim 35 wherein the binding agent is a member selected from the group consisting of silica, methyl cellulose and alumina.

37. The method defined in claim 35 wherein the solvent is a member selected from the group consisting of ethanol, propanol, isopropanol, and butanol, and mixtures thereof.

38. The method defined in claim 29 wherein the oxidative dehydrogenation catalyst has a surface area of from 30 $M^2/g$ to 450 $M^2/g$, a pore volume of from 0.10 cc/g to 0.80 cc/g, and a compacted bulk density of 0.50 g/cc to 1.50 g/cc.

39. The method described in claim 29 wherein the crystalline silica is silicalite.

40. The method described in claim 35 wherein the crystalline silica is silicalite.

41. A method of preparing an alkali metal, vanadium, phosphorus, tin, oxygen and silicalite dehydrogenation catalyst having a surface area of from 30 $M^2/g$ to 450 $M^2/g$, a pore volume of from 0.10 cc/g to 0.80 cc/g, and a compacted bulk density of from 0.50 g/cc to 1.50, which comprises:
 (A) Contacting potassium metaphosphate, ammonium metavanadate, phosphoric acid and stannous chloride at an atomic range of from 0.10:0.10:1:0.001 to 2:1:1:0.30 with aqueous hydrochloric acid at a temperature of from 100° F. to 220° F., and a pressure of from atmospheric pressure to 50 p.s.i.g., to form a catalyst precursor, wherein the vanadium has an average oxidation state of from +3.50 to +4.95;
 (B) admixing from 15 weight percent to 50 weight percent of said catalyst precursor and from 50 weight percent to 85 weight percent of crystalline silica, with from about 0 to 10 weight percent of a binding agent selected from the group consisting of silica, methyl cellulose and alumina and mixtures thereof, and a solvent selected from the group consisting of ethanol, propanol, isopropanol, and butanol and mixtures thereof in a binding agent and solvent weight ratio of from 1:20 to 20:1 to form an impregnated cryatalline silica; and
 (C) calcining the oxidation catalyst at a temperature in the range of from 400° F. to 1,200° F., for ¼ hour to 6 hours.

* * * * *